(12) United States Patent
Wong

(10) Patent No.: US 7,834,059 B2
(45) Date of Patent: Nov. 16, 2010

(54) TOPICAL NEPAFENAC FORMULATIONS

(75) Inventor: Warren Wong, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 425 days.

(21) Appl. No.: 11/292,484

(22) Filed: Dec. 2, 2005

(65) Prior Publication Data

US 2006/0122277 A1    Jun. 8, 2006

Related U.S. Application Data

(60) Provisional application No. 60/632,562, filed on Dec. 2, 2004.

(51) Int. Cl.
*A61K 31/195* (2006.01)

(52) U.S. Cl. .................. 514/567; 424/486

(58) Field of Classification Search .......... 514/567
See application file for complete search history.

(56) References Cited

U.S. PATENT DOCUMENTS

| | | | | |
|---|---|---|---|---|
| 3,828,093 | A | 8/1974 | Bays et al. ............ | 260/469 |
| 4,045,576 | A | 8/1977 | Welstead, Jr. et al. ...... | 424/309 |
| 4,126,635 | A | 11/1978 | Welstead, Jr. et al. ...... | 562/441 |
| 4,182,774 | A | 1/1980 | Welstead, Jr. et al. ...... | 424/309 |
| 4,254,146 | A | 3/1981 | Walsh .................. | 424/309 |
| 4,313,949 | A | 2/1982 | Shanklin, Jr. et al. ...... | 424/248 |
| 4,503,073 | A | 3/1985 | Walsh et al. ............ | 514/539 |
| 4,568,695 | A | 2/1986 | Moran et al. ............ | 514/648 |
| 4,683,242 | A | 7/1987 | Poser .................. | 514/539 |
| 4,783,487 | A | 11/1988 | Brune .................. | 514/563 |
| 4,851,443 | A | 7/1989 | Brune .................. | 514/563 |
| 4,910,225 | A | 3/1990 | Ogawa et al. ............ | 514/561 |
| 5,073,641 | A | 12/1991 | Bundgaard et al. ........ | 560/56 |
| 5,461,081 | A | 10/1995 | Ali et al. ............... | 514/772.3 |
| 5,475,034 | A | 12/1995 | Yanni et al. ............ | 514/619 |
| 5,521,222 | A | 5/1996 | Ali et al. ............... | 514/772.5 |
| 5,624,893 | A | 4/1997 | Yanni .................. | 514/21 |
| 6,342,524 | B1 | 1/2002 | Hellberg et al. .......... | 514/530 |
| 6,638,976 | B2 | 10/2003 | Gamache et al. .......... | 514/532 |
| 2002/0037929 | A1* | 3/2002 | Kapin et al. ............ | 514/619 |
| 2003/0207941 | A1 | 11/2003 | Bingaman et al. ......... | 514/567 |
| 2005/0239895 | A1 | 10/2005 | Sawa et al. ............. | 514/567 |

FOREIGN PATENT DOCUMENTS

| | | |
|---|---|---|
| GB | 2 071 086 A | 9/1981 |
| GB | 2 093 027 A | 8/1982 |
| WO | WO 02/13805 A2 | 2/2002 |
| WO | WO 03/092669 A2 | 11/2003 |

OTHER PUBLICATIONS

Penn et al. Studies of the Effect and Mechanism of Action of Topical Nepafenac in Rat Model of ROP. ARVO Annual Meeting, Abstract No. 2741, (2002).*

Sancilio et al., "AHR-10037, a non-steroidal anti-inflammatory compound of low gastric toxicity," *Agents and Actions*, vol. 31, pp. 117-126 (1990).

Ke et al., "Nepafenac, A Unique Nonsteroidal Prodrug with Potential Utility in the Treatment of Trauma-Induced Ocular Inflammation," *Inflammation*, vol. 24(4), pp. 371-384 (2000).

Walsh et al., "Antiinflammatory Agents. 3. Synthesis and Pharmacological Evaluation of 2-Amino-3-benzoyl phenylacetic Acid and Analogues," *J. Med. Chem.* vol. 27(11), pp. 1379-1388 (1984).

Walsh et al., "Antiinflammatory Agents. 4. Syntheses and Biological Evaluation of Potential Prodrugs of 2-Amino-3-benzoylbenzeneacetic Acid and 2-Amino-3-(4-chlorobenzoyl)benzeneacetic Acid," *J. Med. Chem.*, vol. 33, pp. 2296-2304 (1990).

Penn et al., "Studies of the Effect and Mechanism of Action of Topical Nepafenac in a Rat Model of ROP," *ARVO Annual Meeting*, Abstract No. 2741, 2002.

* cited by examiner

*Primary Examiner*—Jake M. Vu

(74) *Attorney, Agent, or Firm*—Patrick M. Ryan

(57) ABSTRACT

Topical suspension compositions of nepafenac are disclosed. The compositions are especially suitable for topical ophthalmic administration.

2 Claims, No Drawings

TOPICAL NEPAFENAC FORMULATIONS

This application claims priority to U.S. Provisional application, U.S. Ser. No. 60/632,562 filed Dec. 2, 2004.

BACKGROUND OF THE INVENTION

This invention relates to topically administrable ophthalmic formulations of nepafenac. The formulations of the present invention are suspension compositions.

Nepafenac is also known as 2-amino-3-benzoylphenylacetic acid. The topical use of nepafenac and other amide and ester derivatives of 3-benzoylphenylacetic acid to treat ophthalmic inflammation and pain is disclosed in U.S. Pat. No. 5,475,034. According to the '034 patent, compositions containing the 3-benzoylphenylacetic acid derivatives can be formulated into a variety of topically administrable ophthalmic compositions, such as solutions, suspensions, gels or ointments. The compositions optionally contain preservatives, such as benzalkonium chloride, and thickening agents, such as carbomers, hydroxyethylcellulose or polyvinyl alcohol.

SUMMARY OF THE INVENTION

The compositions of the present invention are aqueous suspension compositions of nepafenac. The compositions contain 0.09-0.11% (w/v) nepafenac. The compositions consist essentially of nepafenac, a carbomer, a nonionic surfactant, a tonicity-adjusting agent, a pH-adjusting agent, purified water, and optionally a preservative and a chelating agent.

DETAILED DESCRIPTION OF THE INVENTION

Unless indicated otherwise, all ingredient concentrations are presented in units of % weight/volume (% w/v).

Nepafenac is a known compound. It can be made by known methods. See, for example, U.S. Pat. Nos. 5,475,034 and 4,313,949. The compositions of the present invention contain 0.09-0.11% nepafenac, and preferably 0.1% nepafenac.

In addition to nepafenac, the suspension compositions of the present invention also contain a carbomer as a thickening or physical stability-enhancing agent. Carbomers suitable for use in the present invention are also known as "carboxyvinyl polymers" or carboxypolymethylene. They are commercially available from sources such as Noveon, Inc. (Cleveland, Ohio), which distributes them under the trade name Carbopol®. Carbopol polymers are crosslinked, acrylic acid-based polymers. They are cross-linked with allyl sucrose or allylpentaerythritol. Carbopol copolymers are polymers of acrylic acid, modified by $C_{10-30}$ alkyl acrylates, and crosslinked with allylpentaerythritol. A preferred carbomer for use in the compositions of the present invention is a polymer of acrylic acid cross-linked with allyl sucrose or allylpentaerythritol, which is commercially available as Carbopol® 974P. The concentration of carbomer in the compositions of the present invention will generally range from 0.4-0.6%, and will preferably be 0.5%.

The compositions of the present invention also contain an ophthalmically acceptable nonionic surfactant. Many ophthalmically acceptable nonionic surfactants are known. Suitable nonionic surfactants include, but are not limited to tyloxapol; polyoxyethylene sorbitan esters, such as polysorbate 20, polysorbate 60, and polysorbate 80; polyethoxylated castor oils, such as Cremophor EL; polyethoxylated hydrogenated castor oils, such as HCO-40; and poloxamers. The most preferred surfactant is tyloxapol. In the case of tyloxapol, the surfactant is generally present in an amount of 0.001-0.05%, and preferably 0.01%.

In addition to nepafenac, a carbomer, and a nonionic surfactant, the compositions of the present invention contain an ophthalmically acceptable tonicity-adjusting agent. Ophthalmically acceptable tonicity adjusting agents include, but are not limited to, metal chloride salts and non-ionic tonicity-adjusting agents such as mannitol. Preferred metal chloride salts are those found in human tears, such sodium chloride, potassium chloride, calcium chloride and magnesium chloride. The amount of tonicity adjusting agent contained in the compositions of the present invention is an amount sufficient to cause the composition to have an osmolality of about 250-350 mOsm/kg, preferably 270-315 mOsm/kg. Most preferred is a combination of sodium chloride and mannitol. For the most preferred embodiment where the tonicity adjusting agent is a combination of sodium chloride and mannitol, the amount of sodium chloride is preferably 0.3-0.5% and the amount of mannitol is 2-3%, and the most preferred amount of sodium chloride is 0.4% and the most preferred amount of mannitol is 2.4%.

The compositions of the present invention have a pH from 7.0-7.8. Preferably, the pH of the compositions is 7.3-7.7, and most preferably 7.5. The compositions contain an ophthalmically acceptable pH-adjusting agent in order to achieve the desired pH. Ophthalmically acceptable pH adjusting agents are known and include, but are not limited to, hydrochloric acid (HCl) and sodium hydroxide (NaOH).

The compositions of the present invention optionally contain an ophthalmically acceptable preservative ingredient. Ophthalmically acceptable preservative ingredients are known and include, but are not limited to, benzalkonium halides, such as benzalkonium chloride, polyquaternium-1, and chlorine dioxide. Most preferred are benzalkonium chloride and polyquaternium-1. In the case of benzalkonium chloride, the preservative is preferably present in an amount from 0.001-0.01%, and most preferably 0.005%.

A chelating agent is also optionally included in the suspension compositions of the present invention. Suitable chelating agents include edetate disodium; edetate trisodium; edetate tetrasodium; and diethyleneamine pentaacetate. Most preferred is edetate disodium. If included, the chelating agent will typically be present in an amount from 0.001-0.1%. In the case of edetate disodium, the chelating agent is preferably present at a concentration of 0.01%.

The following examples are intended to illustrate, but not limit, the present invention.

EXAMPLE 1

The formulations shown in Table 1A below were prepared and their in vitro corneal penetration rates compared. Corneal penetration rates were assessed in a perfusion bath using freshly isolated rabbit corneas according to the method described in Ke, et al., *Inflammation*, 24(4):371-384 (2000). The corneal penetration results are shown in Table 1B.

TABLE 1A

| | FORMULATION | |
|---|---|---|
| INGREDIENT | A<br>% (w/v) | B<br>% (w/v) |
| Nepafenac | 0.1 | 0.1 |
| Carbopol 974P | 0.35 | 0.5 |

TABLE 1A-continued

| | FORMULATION | |
|---|---|---|
| INGREDIENT | A % (w/v) | B % (w/v) |
| Sodium Chloride | 0.4 | 0.4 |
| Mannitol | 2.4 | 2.4 |
| Tyloxapol | 0.01 | 0.01 |
| Edetate Disodium | 0.01 | 0.01 |
| Benzalkonium Chloride | 0.01 | 0.01 |
| NaOH/HCl | q.s. pH 7.5 | q.s. pH 7.5 |
| Purified Water | q.s. 100 | q.s. 100 |

TABLE 1B

| FORMULATION | RATE OF CORNEAL PENETRATION (nM/min) (Mean ± SD) |
|---|---|
| A | 10.7 ± 0.6 (n = 4)* |
| B | 17.2 ± 1.2 (n = 4)* |

*Statistically significant difference (p < 0.001).

EXAMPLE 2

The formulations shown in Table 2A below were prepared and their in vitro corneal penetration rates compared. The corneal penetration results are shown in Table 2B.

TABLE 2A

| | FORMULATION | | |
|---|---|---|---|
| INGREDIENT | C % (w/v) | D % (w/v) | E % (w/v) |
| Nepafenac | 0.3 | 0.3 | 0.3 |
| Carbopol 974P | 0.35 | 0.35 | 0.5 |
| Sodium Chloride | 0.4 | 0.4 | 0.4 |
| Mannitol | 2.4 | 2.4 | 2.4 |
| Tyloxapol | 0.01 | 0.01 | 0.01 |
| Edetate Disodium | 0.01 | 0.01 | 0.01 |
| Benzalkonium Chloride | 0.005 | 0.01 | 0.01 |
| NaOH/HCl | q.s. pH 7.5 | q.s. pH 7.5 | q.s. pH 7.5 |
| Purified Water | q.s. 100 | q.s. 100 | q.s. 100 |

TABLE 2B

| FORMULATION | RATE OF CORNEAL PENETRATION (nM/min) (Mean ± SD) |
|---|---|
| C | 63.8 ± 8.9 (n = 4)* |
| D | 65.2 ± 15.0 (n = 3)* |
| E | 61.4 ± 10.5 (n = 5)* |

*No statistical difference among Formulations C, D, and E.

EXAMPLE 3

The formulations shown in Table 3A below were prepared and their in vitro corneal penetration rates compared. The corneal penetration results are shown in Table 3B.

TABLE 3A

| | FORMULATION | | |
|---|---|---|---|
| INGREDIENT | F % (w/v) | G % (w/v) | H % (w/v) |
| Nepafenac | 0.1 | 0.1 | 0.1 |
| Carbopol 974P | 0.35 | 0.35 | 0.5 |
| Sodium Chloride | 0.4 | 0.4 | 0.4 |
| Mannitol | 2.4 | 2.4 | 2.4 |
| Tyloxapol | 0.01 | 0.01 | 0.01 |
| Edetate Disodium | 0.01 | 0.01 | 0.01 |
| Benzalkonium Chloride | 0.005 | 0.01 | 0.01 |
| NaOH/HCl | q.s. pH 7.5 | q.s. pH 7.5 | q.s. pH 7.5 |
| Purified Water | q.s. 100 | q.s. 100 | q.s. 100 |

TABLE 3B

| FORMULATION | RATE OF CORNEAL PENETRATION (nM/min) (Mean ± SD) |
|---|---|
| F | 13.9 ± 4.4 (n = 4)* |
| G | 9.9 ± 5.87 (n = 4)** |
| H | 20.8 ± 2.4 (n = 5) |

*Statistically significant difference between formulations F and H (p = 0.02).
**Statistically significant difference between Formulations G and H (p = 0.007).
No statistically significant difference between Formulations F and G.

EXAMPLE 4

The formulations shown in Table 4A below were prepared and their in vitro corneal penetration rates compared. The corneal penetration results are shown in Table 4B.

TABLE 4A

| | FORMULATION | |
|---|---|---|
| INGREDIENT | I % (w/v) | J % (w/v) |
| Nepafenac | 0.1 | 0.1 |
| Carbopol 974P | 0.35 | 0.5 |
| Sodium Chloride | 0.4 | 0.4 |
| Mannitol | 2.4 | 2.4 |
| Tyloxapol | 0.01 | 0.01 |
| Edetate Disodium | — | — |
| Benzalkonium Chloride | — | — |
| NaOH/HCl | q.s. pH7.5 | q.s. pH7.5 |
| Purified Water | q.s. 100 | q.s. 100 |

TABLE 4B

| FORMULATION | RATE OF CORNEAL PENETRATION (nM/min) (Mean ± SD) |
|---|---|
| I | 12.0 ± 1.9 (n = 4)* |
| J | 18.3 ± 2.2 (n = 4)* |

*Statistically significant difference (p = 0.005).

The data in Examples 1-4 demonstrate that for compositions with nepafenac concentrations of 0.3%, the amount of carbomer had no statistically significant effect on the rate of corneal penetration. In contrast, for compositions with nepafenac concentrations of 0.1%, the amount of carbomer had a statistically significant effect. For compositions containing 0.1% nepafenac, those with a carbomer concentration of 0.5% had a superior rate of corneal penetration compared to compositions containing a carbomer concentration of 0.35%.

EXAMPLE 5

| Topical Ophthalmic Composition | |
|---|---|
| Ingredient | % (w/v) |
| Nepafenac | 0.1 |
| Benzalkonium Chloride | 0.005 |
| Carbomer 974P | 0.5 |
| Tyloxapol | 0.01 |
| Edetate Disodium | 0.01 |
| Mannitol | 2.4 |
| Sodium Chloride | 0.4 |
| NaOH/HCl | q.s. pH 7.3-7.7 |
| Purified Water | q.s. to 100 |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating ophthalmic inflammatory disorders in a human patient comprising topically administering to the patient a composition consisting of
   a) 0.1% (w/v) nepafenac;
   b) 0.5% (w/v) carbomer;
   c) 0.01% (w/v) tyloxapol;
   d) 0.4% (w/v) sodium chloride;
   e) 2.4% (w/v) mannitol;
   f) a pH-adjusting agent in an amount sufficient to cause the composition to have a pH of 7.3-7.7;
   g) 0.005% (w/v) benzalkonium chloride;
   h) 0.01% edetate disodium; and
   i) purified water.

2. In a method of treating ophthalmic inflammatory disorders in a human patient comprising topically administering to the patient an aqueous suspension composition comprising nepafenac, the improvement wherein the composition consists of
   a) 0.1% (w/v) nepafenac;
   b) 0.5% (w/v) carbomer;
   c) 0.01% (w/v) tyloxapol;
   d) 0.4% (w/v) sodium chloride;
   e) 2.4% (w/v) mannitol;
   f) a pH-adjusting agent in an amount sufficient to cause the composition to have a pH of 7.3-7.7;
   g) 0.005% (w/v) benzalkonium chloride;
   h) 0.01% edetate disodium; and
   i) purified water.

* * * * *